United States Patent [19]

Nestler et al.

[11] Patent Number: 4,920,115
[45] Date of Patent: Apr. 24, 1990

[54] METHOD OF LOWERING LDL CHOLESTEROL IN BLOOD

[75] Inventors: John E. Nestler, Richmond, Va.; Cornelius O. Barlascini, Columbus, Ga.; John N. Clore; William G. Blackard, both of Richmond, Va.

[73] Assignee: Virginia Commonwealth University, Richmond, Va.

[21] Appl. No.: 291,149

[22] Filed: Dec. 28, 1988

[51] Int. Cl.$^5$ .............................................. A61K 31/56
[52] U.S. Cl. ..................................... 514/178; 514/824
[58] Field of Search ................................. 514/178, 824

[56] References Cited

U.S. PATENT DOCUMENTS

| | | | |
|---|---|---|---|
| 3,271,250 | 9/1966 | Kanazawa et al. | 514/178 |
| 3,925,480 | 12/1975 | Gastambide et al. | 260/586 E |
| 4,602,008 | 7/1986 | Kreck | 514/178 |
| 4,666,898 | 5/1987 | Coleman et al. | 514/177 |
| 4,680,289 | 7/1987 | Applezweig | 514/172 |

OTHER PUBLICATIONS

Nestler JE, Barlascini CO, Clore JN, Blackard WG, Dehydroepiandrosterone Reduces Serum Low Density Lipoprotein Levels and Body Fat but does not Alter Inuslin Sensitivity in Normal Men, J. Clin Endocrinol Metab, 66: 57-61, 1988.

Nestler JE, Barlascini CO, Clore JN, Blackard WG, Ginsberg HN, Arad Y: Effect of Dehydroepiandrosterone (DHEA) on Serum Apolipoprotein B (apoB) Levels and Low Density Lipoprotein (LDL), Particle Size in Normal Men, Clin. Res. 37: 22A (Abstracts), 1989.

Nestler JE, Clore JN, Strauss III JF, Blackard WG: The Effects of Hyperinsulinemia on Serum Testosterone, Progesterone, Dehydroepiandrosterone Sulfate, and Cortisol Levels in Normal Women and in a Woman with Hyperandrogenism, Insulin Resistance, and Acanthosis Nigricans, J. Clin Endocrinol Metab, 64: 180-184, 1987.

Schwartz AG: Inhibition of Spontaneous Breast Cancer Formation in Femal C3H (A$^{vy}$/a) Mice by Long-Term Treatment with Dehydroepiandrosterone, Cancer Res 39: 1129-1132, 1979.

Ben-David M, Dikstein S, Bismuth G, Sulman FG. Anti-Hypercholesterolemic Effect of Dehydroepiandrosterone in Rats, Proc Soc Exp Biol Med, 125; 1136-1140, 1967.

Coleman DL, Leiter EH, Schwizer RW: Theraputic Effects of Dehydorepiandrosterone (DHEA) in Diabetic Mice, Diabetes 31: 830-833.

Coleman, DL, Schwizer RW, Leiter EH: Effect of Genetic Background on the Therapeutic Effects of Dehydroepiandrosterone (DHEA) in Diabetes-Obesity Mutants and in Aged Normal Mice, Diabetes: 33: 26-32 1984.

Parker, Jr. CR, Simpson ER, Bilheimer DW, Leveno K, Carr BR, MacDonald PC: Inverse Relation Between Low-Density Lipoprotein-Cholesterol and Dehydroepiandrosterone Sulfate in Human Fetal Plasma, Science 208: 512-513, 1980.

Barrett-Connor E, Khaw K-T, Yen SSC: A Prospective Study of Dehydroepiandrosterone Sulfate, Mortality and Cardiovascular Disease, N. Eng J Med, 315: 1519-1524, 1986.

Rizza RA, Mandarino LJ, Gerich JE: Dose-Response Characterisitcs for Effects of Insulin on Production and Utilization of Glucose in Man. Am J Physiol 240: E630-E639, 1981.

(List continued on next page.)

Primary Examiner—H. M. S. Snead
Assistant Examiner—James Saba
Attorney, Agent, or Firm—Whitham & Marhoefer

[57] ABSTRACT

Therapeutic amounts of DHEA are administered to human patients for the treatment and prevention of such disorders as atherosclerosis, angina, diabetes, obesity and congestive heart failure. Administering therapeutic quantities of DHEA to human patients has been found to reduce body fat mass and increase muscle mass, lower serum LDL cholesterol levels, lower serum apoB levels, and not affect tissue sensitivity to insulin.

8 Claims, 1 Drawing Sheet

OTHER PUBLICATIONS

Morgan CR, Lazarow A: Immunoassay of Insulin: Two Antibody System, Diabetes 12: 115—126, 1963.

Resko JA, Ellinwood WE, Pasztor LM, Buhl AE: Sex Steriods in the Umbilical Circulation of Fetal Rhesus Monkeys from the time of Gonadal Differentiation, J. Clin Endocrinol Metab. 50: 900–905, 1980.

Plymate SR, Fariss BL, Bassett ML, Matej L: Obesity and its Role in Polycystic Ovary Syndrome. J. Clin. Endocrinol Metab 52: 1246-1248, 1981.

Segal P, Bachorik PS, Rifkind BM, Levy RI: Lipids and Dyslipoproteinemia, In: Henry JB (ed), Clinical diagnosis and Management by Laboratory methods, Saunders, Philadelphia, 1984, pp. 180–203.

Kent S: DHEA: "Miracle Drug?", Geriatrics 37: 157–161 1982.

Moordian AD, Morley JE, Korenman SG: Biological Actions of Androgens, Endocr Rev, 8: 1-28, 1987.

METHOD OF LOWERING LDL CHOLESTEROL IN BLOOD

This invention was made with U.S. Government support under contracts RR00065 and AM07428 awarded by the National Institutes of Health. The government has certain rights in this invention.

BACKGROUND OF THE INVENTION

1. Field of the Invention

The subject invention is directed to using pharmacological quantities of hormones to prevent the development of atherosclerosis and, more particularly, to the administration of dehydroepiandrosterone (DHEA) for beneficial effects in human beings.

2. Description of the Prior Art

Cholesterol plays an essential role in the body in building cell membranes, in sex hormones, and in aiding digestion. Cholesterol is produced in the liver and transported to cells via the bloodstream, but it may also be obtained directly from fatty foods typically found in western diets. The low density lipoprotein (LDL) carrier particles carry 60-80% of the blood's total cholesterol. An excess of LDL carrier particles may lead to plaque build up on the interior walls of coronary arteries.

Blockage of the artery causes angina (chest pain) and over time, large build ups can lead to heart attacks. The condition of having plaque on the artery walls is refereed to as atherosclerosis. Severe cases of atherosclerosis are treated by mechanically compressing the plaque on the walls with an inflatable balloon by balloon angioplasty. The high density lipoprotein (HDL) carrier particles remove excess cholesterol from the blood and tissue cells and may collect cholesterol from plaque, thus reversing the process of "narrowing" the artery. For those at risk, the typical approach for correcting problems associated with plaque build up is to decrease the total cholesterol level. This may be done using any of a variety of well known methods including changing one's diet.

DHEA is the most abundantly produced adrenal steroid, and serum concentrations of its sulfate ester, DHEA sulfate (DHEA-S), are approximately twenty fold higher than those of any other circulating steroid hormone. Peak serum DHEA and DHEA-S levels occurs when patients are approximately twenty-five years old. The serum levels decrease with age and are approximately five percent of the peak level when patients are between eighty-five and ninety years old. Both DHEA and DHEA-S can be converted to testosterone. All tissues studied to date contain steroid sulfatases which readily convert DHEA-S to DHEA, and DHEA have a high turnover rate. Despite the abundance and rapid turnover of the hormone, the physiological role of DHEA is unknown.

In *Geriatrics* 37: 157 (1982), DHEA was reported to be a "miracle drug" which may prevent obesity, aging, diabetes mellitus and heart disease. These assertions stem from animal studies which demonstrated that DHEA administration resulted in lower body weight in C3H(Avy/a) mice without affecting appetite or food intake, prevented the development of diabetes in genetically diabetic (−db/db) or obese (−ob/ob) mice, increased tissue sensitivity to insulin in aged normal mice, and prevented the rise in cholesterol levels of rats made hypothyroid with propylthiouracil. Human studies have revealed an inverse correlation between fetal serum DHEA-S and low density lipoprotein (LDL) levels (Parker et al, *Science* 208: 512 (1980)), and an inverse relationship between cardiovascular death and serum DHEA-S levels in adult men (Barrett-Connor et al, *N. Engl. J. Med.*, 315: 1519 (1986). DHEA was widely used in this country for weight loss, longevity and sex life enhancement purposes until it was recently banned for nonprescription sales by the Food and Drug Administration.

U.S. Pat. No. 4,602,008 to Krsek, U.S. Pat. No. 4,666,898 to Coleman et al, and U.S. Pat. No. 4,680,289 to Applezweig show synthesized metabolites of DHEA called etiocholanolones which are used to treat obesity. These metabolities are not converted into sex hormones by the body. It is believed that a balance exists in the body between DHEA and cortisol. DHEA tends to limit production of stored compounds like fat, while cortisol promotes such production. As the level of DHEA declines with age, so does its opposing effect to cortisol. This decline leads to the chronic diseases of aging, including atherosclerosis, diabetes, obesity and cancer. Studies using mice have shown that obese mice treated with ethiocholanolones can attain their normal weight in a short period of time.

SUMMARY OF THE INVENTION

It is an object of this invention to provide a method for selectively reducing the LDL cholesterol without reducing the HDL cholesterol.

It is another object of this invention to provide a method for reducing apolipoprotein B (apoB) levels in a patient.

It is yet another object of this invention to administer therapeutic amounts of DHEA to human patients for the treatment and prevention of such disorders as atherosclerosis, angina, diabetes, obesity and congestive heart failure.

According to the invention, administering therapeutic quantities of DHEA to human patients has been found to reduce body fat mass and increase muscle mass, lower serum LDL cholesterol levels, lower serum apoB levels, and not affect tissue sensitivity to insulin.

BRIEF DESCRIPTION OF THE DRAWINGS

The foregoing and other objects, aspects and advantages of the invention will be better understood from the following detailed description of a preferred embodiment of the invention with reference to the accompanying drawing in which the sole FIGURE shows a bar graph contrasting the glucose disposal rate of the subject groups at day 0 and day 28 in the study.

DETAILED DESCRIPTION OF THE PREFERRED EMBODIMENT OF THE INVENTION

Figure 1:
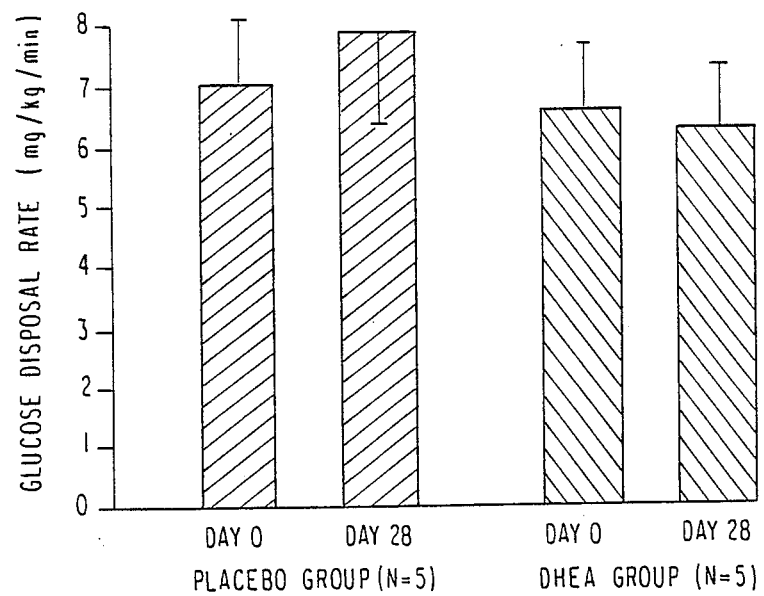

The inventor has conducted a prospective, randomized, double blind study in which normal men received either DHEA or a placebo for twenty-eight days. The dosage of DHEA used in the study was 400 milligram of DHEA four times a day. Before and after DHEA or placebo administration, anthropometric parameters, serum lipid and apoB levels, and tissue sensitivity to insulin were determined. Ten normal men were divided into two age matched and weight matched groups. The five men in the "placebo group" has a mean age of $24.5 \pm 1.1$ years with a range of 22.4 to 25.2 years. The five men in the "DHEA group" had a mean age of 23.7±0.9 years with a range of 22.4 to 25 years. The range of body mass index (BMI) values was similar in both groups with the placebo group having a BMI ranging between 20.5 and 29.3 kilograms per meter squared (kg/m$^2$) and the DHEA group having a BMI ranging between 20.0 and 30.0 kg/m$^2$. None of the men were taking any medications and none had a family history of diabetes mellitus. The study was approved by the committee on the Conduct of Human Research of the Medical College of Virginia, and informed consent was obtained from each man in the study.

In Nestler et al, *J. Clin. Endocrinol. Metab.*, 64: 180 (1987), the inventor found a decline in serum DHEA-S levels in women during supraphysiological hyperinsulinemia. This observation coupled with the demonstration that DHEA increases insulin sensitivity of aged normal mice (Coleman et al, *Diabetes*, 33: 26 (1984)) suggested to him that DHEA may be an endogenous regulator of tissue sensitivity to insulin. The beneficial effects of DHEA on obesity, diabetes, and lipids might be done to its effect on insulin sensitivity. This study was designed to test that hypothesis in a prospective manner, using the hyperinsulinemic euglycemic clamp technique as a measure of insulin sensitivity. All hormone, SHBG, and lipid measurements from an individual man were determined in duplicate in a single assay. The intra-assay coefficient of variation of all assays was less than eight percent. All results were reported as mean±SEM. When comparisons within a group were made, data were analyzed using the Students two tailed paired t test. When comparisons between groups were made, the Students two tailed unpaired t test was used. $P<0.05$ was considered significant.

On the first day of the study (day 0), blood samples were taken for determination of serum steroid, sex hormone binding globulin (SHBG), lipid, glucose, apoB and insulin concentrations. Each of the men had fasted from the night before. Tissue sensitivity to insulin was assessed using the hyperinsulinemic-euglycemic clamp technique. The men took orally, in a double blind fashion, capsules containing either placebo or 400 milligrams (mg) of DHEA four times daily for twenty-eight days. The total daily DHEA dose was 1600 mg or 5.55 millimoles (mmol). They were not instructed to change their lifestyle or diets in any way. Although activity level and diet were not monitored, at the conclusion of the study each man denied any changes in these parameters. No side effects were noted in either group. The men returned on days 7, 14, and 21 for repeat measurements of DHEA-S levels. On day 28, the day 0 studies were repeated.

Table 1 shows anthopometric measurements for the study before and after placebo or DHEA administration.

TABLE 1

ANTHROPOMETRIC PARAMETERS ON DAY 0 AND DAY 28

| Parameter | Placebo Group | | DHEA Group | |
|---|---|---|---|---|
| | day 0 | day 28 | day 0 | day 28 |
| Wt (kg) | 75.7 ± 7.0 | 74.3 ± 7.0 | 77.5 ± 3.4 | 78.2 ± 3.5 |
| BMI (kg/m$^2$) | 24.6 ± 1.6 | 24.7 ± 1.5 | 23.9 ± 1.7 | 24.1 ± 1.7 |
| % Body Fat | 16.9 ± 3.5 | 16.7 ± 2.2 | 15.9 ± 3.7 | 10.9 ± 1.2 |

The anthropometric parameters were measured within one week before day 0 of the study and within one week after day 28. All measurements were made by the same investigators. The men were weighed in both air and water using the techniques disclosed in Behnke et al, *JAMA* 118: 495 (1942), this article being incorporated herein by reference. The water measurements were done at maximal exhalation, and a correction factor of 1.45 liters (L) was used to account for residual air. A 9.09 kg weight was attached to each man to negate any buoyancy. Using the general formula for specific gravity, densities were obtained. Percent body fat was determined according to the techniques disclosed in Siri, *Proceedings of the Conference, Jan.* 22–23 (1959) *National Academy of Sciences*, this article being herein incorporated by reference. Percent body fat is equal to [(4.95/density)-4.50]*100.

Serum DHEA-S levels were determined using a commercial antibody coated tube kit available from the Pantex company of California. Table 2 shows the effect of DHEA administration on serum DHEA-S levels.

TABLE 2

Serum DHEA-S Concentrations in the Study Subjects

| Group | DHEA-S (μmol/L) | | | | |
|---|---|---|---|---|---|
| | Day 0 | Day 7 | Day 14 | Day 21 | Day 28 |
| Placebo | 9.9 ± 1.5 | 10.7 ± 2.6 | 11.0 ± 2.2 | 10.4 ± 2.3 | 8.7 ± 1.7 |
| DHEA | 10.9 ± 1.9 | 33.1 ± 7.6 | 39.7 ± 12.5 | 30.6 ± 9.3 | 38.8 ± 11.2 |

Weekly mean serum DHEA-S levels did not change in the placebo group, but rose 2.5 to 3.5 fold in the DHEA group. Referring back to table 1, no change in anthropometric measurements occurred in the placebo group; however, in the DHEA group, the percent body fat decreased in four of the five men, with a mean decrease of 31%. The single man in the DHEA group who did not lose body fat was the leanest subject in that group (BMI=20.0 kg/m$^2$) and weighed about 90% of the ideal body weight. No weight change occurred in the DHEA group. The reduction in the body fat mass by DHEA may in part depend upon pre-existing adiposity since the maximal reduction in body fat occurred in the most obese man, whereas the single man that did not lose body fat was the leanest. The decrease in percent body fat in the absence of weight change suggests an increase in muscle mass coupled with a reduction in fat mass. Pharmocological doses of other androgens have had similar results (Mooradian et al., *Endocr. Rev.* 8: 1 (1987)). It is believed androgens produce skeletal muscle cell hyperplasia by direct interaction with the testosterone receptor, whereas the reduction in fat is due to their aromatization to estrogens in adipose tissue.

Serum total cholesterol and triglyceride levels were measured using established enzymatic methods which are discussed by Segal et al, in *Clinical Diagnosis and Management by Laboratory Methods*, published in 1984, p. 186. After precipitation of other lipid components with sodium phosphotungstate, HDL cholesterol was measured enzymatically. Very low density lipoprotein (VLDL) cholesterol levels were calculated using the formula: VLDL cholesterol=triglycerides/5. LDL chlolesterol levels were calculated using the formula: LDL cholesterol=total cholesterol−HDL cholesterol−VLDL cholesterol. Serum apoB was analyzed using specific RIA as described in Gibson et al, *J Lipid Res.*, 24: 886 (1983), and this reference is herein incorporated by reference.

Tables 3 and 4 show the effect of DHEA administration on measured serum total cholesterol, HDL cholesterol, LDL cholesterol, VLDL cholesterol, triglyceride concentrations, and apoB.

TABLE 3

| Serum Concentrations in the Study Subjects | | |
|---|---|---|
| | Placebo Group | |
| | Day 0 | Day 28 |
| Total Cholesterol (mmol/L) | 4.73 ± 0.34 | 4.66 ± 0.37 |
| HDL Cholesterol (mmol/L) | 1.24 ± 0.04 | 1.12 ± 0.05 |
| LDL Cholesterol (mmol/L) | 3.04 ± 0.39 | 3.10 ± 0.34 |
| VLDL Cholesterol (mmol/L) | 0.45 ± 0.04 | 0.43 ± 0.05 |
| Triglyceride (mmol/L) | 0.98 ± 0.08 | 0.96 ± 0.11 |
| apoB (μg/ml) (P = 0.27) | 1136.4 ± 181.6 | 950.1 ± 81.4 |

TABLE 4

| Serum Concentrations in Study Subjects | | |
|---|---|---|
| | DHEA Group | |
| | Day 0 | Day 28 |
| Total Cholesterol (mmol/L) | 4.82 ± 0.21 | 4.48 ± 0.29$^a$ |
| HDL Cholesterol (mmol/L) | 1.09 ± 0.11 | 1.01 ± 0.09 |
| LDL Cholesterol (mmol/L) | 3.21 ± 0.11 | 2.97 ± 0.14$^b$ |
| VLDL Cholesterol (mmol/L) | 0.53 ± 0.10 | 0.50 ± 0.11 |
| Triglycerides (mmol/L) | 1.14 ± 0.22 | 1.07 ± 0.23 |
| apoB (μg/ml) (P < 0.01) | 1229.1 ± 107.9 | 934.1 ± 55.8 |

$^a$ P < 0.05 compared to day 0 value of DHEA group
$^b$ P < 0.01 compared to day 0 value of DHEA group Referring to Table 3, serum total cholesterol, HDL cholesterol, LDL cholesterol, VLDL cholesterol, triglyceride, and apoB concentrations did not change significantly in the placebo group. Referring to Table 4, the mean total cholesterol concentration dropped 7.1% (P<0.05) in the DHEA group and the mean serum LDL cholesterol concentration dropped 7.5% (P<0.01). Mean serum HDL cholesterol, VLDL cholesterol, and triglyceride concentrations did not change in the DHEA group. The fall in serum LDL cholesterol in the DHEA group assumes that DHEA administration did not alter the composition (i.e., triglyceride to cholesterol mass ratio) of VLDL particles. The finding of a significant drop in total serum cholesterol due almost entirely to decreases in LDL cholesterol in normal men contrasts significantly with animal studies, in which DHEA prevented the rise in serum cholesterol in rats made hypothyroid with propylthiouracil, but had no effect on serum cholesterol levels in normal rats (Ben-David et al, *Proc. Soc. Exp. Biol. Med.* 125: 1136 (1967)). The magnitude of serum cholesterol reduction by DHEA in the inventor's study represents an estimated 14% reduction in risk for the development of cardiovascular disease. The derived reduction of coronary heart disease from the reduction of cholesterol is discussed in the Lipid Research Clinics article, *JAMA*, 251: 365-3/4 (1984), and this reference is herein incorporated by reference. The DHEA induced fall in serum LDL cholesterol coupled with the inverse correlation between fetal serum DHEA-S and LDL levels reported by Parker et al, *Science* 208: 512 (1980), suggest that a decrease in this risk factor could conceivably play a role in the reported decreased risk of cardiovascular death in men with higher levels (Barret-Connor et al., *N. Engl. J. Med.* 315: 1519 (1986)). The reduction in serum LDL cholesterol levels and the absence of effect on serum HDL levels contrasts markedly with the effects of other androgens on lipids. Androgens typically raise serum LDL cholesterol levels and reduce serum HDL levels (Mooradian et al, *Endocr. Rev.* 8: 1 (1987)). These changes are believed to account at least in part of the increased risk for atherosclerosis and cardiovascular disease in men treated with anabolic steroids. The fall in serum LDL cholesterol shown in Table 4 is more analogous to an estrogen effect than an androgen effect.

Furthermore, the serum apoB fell in all five men in the DHEA group with a signicant decrease in mean serum apoB of 24% (P<0.01). The serum apoB increased in two men and fell in three men in the placebo group with no significant change in serum apoB for the group as a whole. Serum apoB may be a better predictor of the severity of clinical coronary artery disease than levels of total cholesterol or LDL cholesterol. The importance of apoB in causing atherosclerosis is discussed in Brunzell et al, *Arterosclerosis*, 4: 79 (1984), and this article is incorporated herein by reference. A DHEA associated fall in serum apoB may in part contribute to the apparent anti-atherogenic action of DHEA.

Serum glucose concentrations were determined by the glucose oxidase method. Serum insulin levels were determined by RIA as discussed in Morgan et al, *Diabetes* 12: 115 (1963), this article being incorporated herein by reference. The hyperinsulinemic-euglycemic clamp technique for tissue sensitivity to insulin was performed according to the following method. Catheters were inserted into the right antecubital vein for infusion of insulin and glucose and into the left antecubital vein for blood withdrawal. Human regular insulin, available from the Novolin company of New Jersey, was infused via a Harvard pump, available from Harvard Apparatus of Massachusetts, at a rate of 4.0 milli-units (mU) per kg per min which is 29 picomoles (pmol)/kg*min. for 2 min. followed by 2.0 mU/kg*min. which is 14 pmol/kg*min. for 6 min. and then at 1 mU/kg*min. which is 7 pmol/kg*min. for the remainder of the study. Serum glucose was kept constant at the fasting level by bedside serum glucose determinations every 5 min. and appropriate adjustment of a variable infusion of 25% glucose. The clamp was maintained for 120 minutes, and the average glucose infusion rate required to maintain euglycemia during the last 30 min. of the clamp was used as the index of tissue sensitivity to insulin (M). It was assumed that endogenous glucose production was negligible during this time period. The mean coefficient of variation for the clamp studies performed on day 0 was 6.4% (n=10). The mean coefficient of variation for the clamp studies performed on day 28 was 6.0% (n=10).

The day 0 and day 28 mean fasting serum glucose levels were similar in both the placebo group (5.0±0.2 vs. 5.4±0.1 mmol/L; P=NS) and the DHEA group (4.9±0.1 vs. 5.1±0.1 mmol/L; P=Ns). Fasting serum insulin levels on day 0 and day 28 were also similar in both groups (placebo group: 118±11 vs. 91+13 pmol/L; P=NS. DHEA group: 105±17 vs. 90±8 pmol/L; P=NS). The drawing FIGURE shows the glucose disposal rates in terms of mg/kg/min for the two groups. To convert the glucose disposal rate to micromoles per kg/min., simply multiply by 5.51. In the placebo group, tissue sensitivities to insulin (M) as measured by the hyperinsulinemic-euglycemic clamp technique on day 0 and day 28 were similar (39.1±5.5 vs. 43.5±8.8 $\mu$mol glucose/kg*min; P=NS). Likewise, tissue sensitivities to insulin were similar on day 0 and day 28 in the DHEA group (36.4±5.0 vs. 34.7±5.5 $\mu$mol glucose/kg*min; P=NS). The day 0 and day 28 steady state insulin levels during the 30 to 120 minute period of the clamp in the placebo group and DHEA group were comparable (placebo group: 494±39 vs. 433±23 pmol/L; P=NS. DHEA group: 462±65 vs. 504±60 pmol/L; P=NS).

Unlike androgen therapy which results in decreased tissue sensitivity to insulin, DHEA administration had no effect on tissue sensitivity to insulin. The hyperinsulinemic-euglycemic clamp studies were not performed at an insulin concentration that would have resulted in maximal glucose uptake. Therefore, insulin responsiveness was not assessed. However, a change in insulin responsiveness seems unlikely in the absence of a change in insulin sensitivity. It is possible that DHEA administration might alter insulin sensitivity if administered for a longer duration or to a group of individuals with pre-existing insulin resistance (e.g., type II diabetic patients).

Serum androstenedione (A), estrone ($E_1$) and 17 beta-estradiol ($E_2$) concentrations were measured by RIA as described in Resko et al, *J. Clin. Endocrinol. Metab.* 50: 900 (1980), this article being herein incorporated by reference. Serum (1.0 mL) was extracted with diethyl ether, and steroids were isolated by sephadex LH-20 column chromatography. Highly specific antisera were used to measure A, $E_1$, and $E_2$. Tritium labeled steroids were added to serum before extraction to account for procedural losses. Serum total testosterone (T) were determined using a commercial RIA kit available from Diagnostic Products of California. SHBG was determined by [$^3$H] dihydrotestosterone saturation as described in Plynate et al, *J. Clin. Endocrinol. Metab.* 52: 1246 (1981), this article being herein incorporated by reference. Free T, which is non-SHBG bound T, was calculated from the total molar concentrations of T and SHBG according to the following modification of mass equation: $(x/T-x)(1/SHBG)=k(1-x/SHBG)$; $x=(b-\sqrt{b^2-4a})/2$, where x is the molar concentration of SHBG bound T, k is the association constant of T and SHBG, a=testosterone*SHBG, and b=1/k+SHBG+testosterone. The modification of mass equation is discussed in Pearlman, *Karolinska Symposia on Research Methods in Reproductive Endocrinology, Huddinga, Sweden, Second Symposium,* 1970, Vol 2: 225, and this reference is herein incorporated by reference.

Tables 5 and 6 show the effects of DHEA administration on serum A, $E_1$, $E_2$, total T, free T, and SHBG concentrations.

TABLE 5

Serum Concentrations in Study Subjects
Placebo Group

|  | Day 0 | Day 28 |
|---|---|---|
| $E_2$ (pmol/L) | 117 ± 18 | 91 ± 11 |
| $E_1$ (pmol/L) | 193 ± 37 | 228 ± 38 |
| A (nmol/L) | 5.5 ± 0.2 | 5.8 ± 0.4 |
| Total T (nmol/L) | 29.0 ± 3.1 | 30.4 ± 2.9 |
| Free T (nmol/L) | 12.9 ± 2.9 | 11.6 ± 2.0 |
| SHBG (mol/L) | 17.9 ± 1.7 | 20.8 ± 1.3 |

TABLE 6

Serum Concentrations in Study Subjects
DHEA Group

|  | Day 0 | Day 28 |
|---|---|---|
| $E_2$ (pmol/L) | 117 ± 26 | 103 ± 6 |
| $E_1$ (pmol/L) | 194 ± 21 | 232 ± 19 |
| A (nmol/L) | 4.3 ± 0.6 | 8.6 ± 1.2* |
| Total T (nmol/L) | 26.6 ± 2.2 | 30.4 ± 4.2 |
| Free T (nmol/L) | 11.0 ± 1.3 | 16.9 ± 2.2 |
| SHBG (nmol/L) | 17.5 ± 3.7 | 13.9 ± 3.0 |

*P < 0.004 compared to day 0 value of DHEA group

Serum A concentrations were similar in the placebo and DHEA groups on day 0, and serum A did not change in the placebo group during the study. In the DHEA group, as shown in Table 6, the serum A concentration increased two fold. Serum $E_1$, $E_2$, total T, free T, and SHBG concentrations did not change in either the placebo or DHEA group. Although serum $E_1$ and $E_2$ did not rise in the DHEA group, it is likely that the significant rises in DHEA-S (see Table 2) and serum A resulted in increased aromatization of these androgens at the tissue level. Although the serum DHEA-S and serum A levels rose in the DHEA group, SHBG levels did not change. Androgens may reduce serum SHBG levels directly and may also reduce serum SHBG indirectly by causing insulin resistance (which results in elevated insulin levels). Insulin per se lowers SHBG levels as well (Plymate, S. R., L. A. Matej, R. E. Jones, and K. E. Friedl, unpublished data). The results of this study are consistent with this possibility, since insulin levels and SHBG levels did not change in the DHEA group.

While the study was conducted with each man ingesting a total of 1600 mgs a day taken as four 400 mg tablets, the optimum therapeutic dose will depend on the patient being treated. As stated earlier, the peak serum DHEA and DHEA-S levels occur when the patient is twenty-five years old and they decrease to approximately five percent of the peak level when the patent is eighty-five years old. The patients in this study had ages ranging between 22.4 to 25 years. If the youngest age of a man in this study is considered, 22.4 years, it can be calculated that his optimum dose will be approximately 1800 mg a day when he reaches age 25 (this being calculated from the following equation: 22.4/1600=25/x; x=1785). When he reaches age 85, his optimum dose will be approximately 100 mg a day (this being calculated from the following equation: 0.05*1800=90). The patients in this study ingested the 400 mg of DHEA in a capsule form having an inert binder. DHEA may also be administered by other well known techniques such as by injection or suppository. It is also believed that the regimen, 400 mg four times a day, can be altered to suit the needs of the patient. The regimen must be chosen to avoid the risks of shock to the patient which may result from too much DHEA at one time.

While the invention has been described in terms of the preferred embodiment of the invention wherein a 1600 mg dose of DHEA per day was effective in selectively lowering serum LDL cholesterol and apoB concentrations, those skilled in the art will recognize that the doses may be altered within the spirit and scope of the appended claims.

Having thus described my invention, what I claim as new and desire to secure by Letters Patent is the following:

1. A method of lowering low density lipoprotein cholesterol concentrations in human beings, comprising a step of administering a therapeutic dose of dehydroepiandrosterone to a patient to lower said low density lipoprotein cholesterol concentration in said patient.

2. A method as recited in claim 1 wherein said therapeutic dose comprises a daily amount of said dehydroepiandrosterone ranging between 100 milligrams and 1800 milligrams.

3. A method as recited in claim 2 wherein said daily amount is approximately 1600 milligrams.

4. A method as recited in claim 2 wherein said daily amount is ingested orally in capsule form wherein said dehydroepiandrosterone is held in an inert binder.

5. A method of lowering apolipoprotein B concentrations in human beings, comprising a step of administering a therapeutic dose of dehydroepiandrosterone to a patient to lower said apolipoprotein B concentration in said patient.

6. A method as recited in claim 5 wherein said therapeutic dose comprises a daily amount of said dehydroepiandrosterone ranging between 100 milligrams and 1800 milligrams.

7. A method as recited in claim 6 wherein said daily amount is approximately 1600 milligrams.

8. A method as recited in claim 6 wherein said daily amount is ingested orally in capsule form wherein said dehydroepiandrosterone is held in an inert binder.

* * * * *